United States Patent [19]
Walliser

[11] 3,986,512
[45] Oct. 19, 1976

[54] OSTEOTOME

[75] Inventor: Anton Walliser, Dornach, Switzerland

[73] Assignee: M. Schaerer A.G., Switzerland

[22] Filed: Dec. 20, 1974

[21] Appl. No.: 534,774

[30] Foreign Application Priority Data
Dec. 21, 1973 Switzerland............ 18056/73

[52] U.S. Cl................ 128/317; 30/393
[51] Int. Cl.² ............ A61B 17/14; B23D 49/08
[58] Field of Search............ 30/393; 128/317

[56] References Cited
UNITED STATES PATENTS

| 2,705,980 | 4/1955 | Papworth | 30/393 |
| 2,961,016 | 11/1960 | Papworth | 30/393 |
| 3,905,105 | 9/1975 | Tuke | 128/317 X |

Primary Examiner—Channing L. Pace
Attorney, Agent, or Firm—Stevens, Davis, Miller & Mosher

[57] ABSTRACT

An osteotome comprising an interchangeable saw-blade, a crank, and a driving shaft makes possible simultaneous reciprocating and vertical swiveling movements of the saw-blade, thus obviating setting of the saw-teeth, enabling narrow cuts to be made in bone, and providing the opportunity for required sterilization and cooling.

3 Claims, 1 Drawing Figure

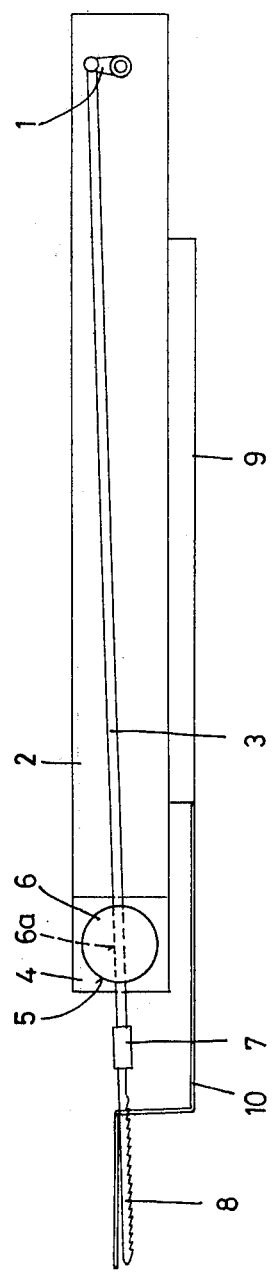

OSTEOTOME

This invention relates to an osteotome.

Osteotomes are already known in the form of oscillating saws in which the saw-blade executes a purely reciprocating movement. In order that the sawdust may be carried off, the teeth of the saw-blade must be set, for otherwise the saw-blade might jam. However, such setting of the teeth results in a comparatively wide kerf, so that these known instruments cannot be used for cutting very thin lamellar bones.

On the other hand, metalworking saws are known in which the saw-blade carries out a movement not only of translation but also of rotation, so that after a sawing stroke, it is lifted off the workpiece and is not set down upon it again until having executed an idling stroke in the opposite direction. However, these rather unwieldy known saws, having a complicated operating control, are not suitable for use as osteotomes even if produced in a smaller size, and above all they cannot fulfill the requirements which osteotomes must meet as to the possibilities of cooling and sterilization.

It is the object of this invention to provide an osteotome which not only can make very thin cuts without any danger of the saw-blade's jamming but is also so simple in its construction that it meets the requirements for easy handling, sterilization, and cooling.

To this end, the osteotome according to the present invention comprises a saw-blade, a crank, and a driving shaft, the driving shaft being swivellably mounted between the crank and the saw-blade, detachably secured to the saw-blade, and driven via the crank, and the swivel axis of the driving shaft intersecting the geometrical axis thereof.

A preferred embodiment of the invention will now be described in detail with reference to the accompanying drawing, which is a diagrammatic view of a vertical section through the osteotome.

In the embodiment illustrated, a crank 1 is driven via suitable transmission means by a motor (not shown). One end of a driving shaft 3, surrounded by a tubular housing 2, is linked to the crank 1. Secured within the housing 2 at the end of it remote from the crank 1 is a bearing block 4 having a spherical inner bearing surface 5 in which a bored bearing ball 6 is pivotably held. Instead of the spherical inner surface 5, a cylindrical one might also be used, in which case the bearing ball 6 would be replaced by a bored cylinder. The bearing ball 6 is preferably made of hard metal, while bearing bronze has proved suitable for the bearing block 4. The driving shaft 3 passes through the bore 6a of the bearing ball 6 in which it is slidingly held, so that the driving shaft 3 is both swivellable and axially displaceable with respect to the bearing block 4.

Attached to the free end of the driving shaft 3 projecting beyond the bearing ball 6 is a connecting piece 7, shown only diagrammatically, for detachably securing a saw-blade 8, which is stiletto-shaped in the embodiment illustrated here. It will be understood, however, that saw-blades of different shape may be used depending upon the type of cut to be made.

When the crank 1 is driven by the motor via the transmission, the driving shaft 3, and with it the saw-blade 8, moves back and forth as well as up and down at the same time owing to the way in which it is mounted, as described above. The direction of rotation of the crank 1 and the direction in which the teeth of the saw-blade 8 are inclined are so chosen that during the retracting movement, the saw-blade 8 is in its lower position, i.e., its cutting position; it is then lifted off the cutting location and moved forward, whereupon it once more drops down onto the cutting location and starts a new cycle by retracting to carry out the sawing operation. Because the saw-blade 8 is always operative only in the direction of retraction and is lifted off the cutting location during each interval, there is an opportunity both for expedient rinsing of the kerf to remove sawdust and for adequate cooling by means of a spray of sterile liquid, for example. Furthermore, the saw-blades 8 designed for use with this driving arrangement may be very narrow, so that the loss of bone substance is decisively lessened, and it thus becomes possible to make extremely narrow cuts without running any risk of jamming.

The entire osteotome can be sterilized, together with the driving unit and the supply cables, and the saw-blade may even be produced in the form of a sterile-packed disposable unit.

Since the saw-blades are interchangeable, they may be of various lengths and have clamping portions of different lengths as well; hence the distance between the centre of the bearing ball 6 and the row of teeth on the saw-blade 8 may be varied for the purpose of producing cuts of various shapes.

Also attached to the housing 2 is a bracket 9 with a support 10 extending into the area of the saw-blade 8. By means of the support 10, the saw can be braced against the bone to be sawn in order to maintain a constant relative position between the bone and the saw.

What is claimed is:

1. An osteotome, comprising:
   an elongated frame;
   a crank member rotatably mounted on said frame;
   a drive shaft having means for detachably mounting a saw blade
   located at one end and having its other end coupled to a radial arm of said crank member;
   a bearing member, having a bore hole extending therethrough, rotatably mounted on said frame with an axis of rotation substantially parallel to the rotational axis of said crank member and axially located between the two ends of said drive shaft, said drive shaft extending through and being slidably movable within said bore hole;
   wherein said shaft is pivotally and axially driven by said crank member; and
   wherein the pivot axis of said drive shaft intersects an axis connecting the centers of rotation of said crank and bearing members.

2. An osteotome in accordance with claim 1, further comprising a support coupled to said frame to be braced against a bone to be cut.

3. An osteotome according to claim 1, wherein the center of pivotal motion of said shaft is substantially coincident with the center of rotational movement of said bearing.